US010689606B2

(12) United States Patent
Chow

(10) Patent No.: US 10,689,606 B2
(45) Date of Patent: Jun. 23, 2020

(54) APPARATUS AND METHOD FOR THREE-DIMENSIONAL (3D) PRINTING/BIO-PRINTING

(71) Applicant: Chun To Chow, Hong Kong (HK)

(72) Inventor: Chun To Chow, Hong Kong (HK)

(*) Notice: Subject to any disclaimer, the term of this patent is extended or adjusted under 35 U.S.C. 154(b) by 0 days.

(21) Appl. No.: 16/217,088

(22) Filed: Dec. 12, 2018

(65) Prior Publication Data
US 2019/0177676 A1 Jun. 13, 2019

Related U.S. Application Data

(60) Provisional application No. 62/597,901, filed on Dec. 12, 2017.

(51) Int. Cl.
*B33Y 30/00* (2015.01)
*C12M 3/00* (2006.01)
(Continued)

(52) U.S. Cl.
CPC ........... *C12M 21/08* (2013.01); *B29C 64/112* (2017.08); *B29C 64/209* (2017.08); *B29C 64/245* (2017.08); *B29C 64/264* (2017.08); *B29C 64/364* (2017.08); *B29C 64/393* (2017.08); *B33Y 30/00* (2014.12); *B33Y 50/02* (2014.12);
(Continued)

(58) Field of Classification Search
CPC ..... C12M 21/08; C12M 33/00; B29C 64/264; B29C 64/112; B29C 64/245; B29C 64/209; B33Y 10/00; B33Y 30/00; B33Y 40/00; B33Y 70/00; B33Y 80/00; B29K 2995/0056
See application file for complete search history.

(56) References Cited

U.S. PATENT DOCUMENTS

2017/0036300 A1* 2/2017 Takashima ........... B23K 26/342
2017/0239718 A1* 8/2017 Steinhoff, Jr. ....... B23K 26/342
(Continued)

FOREIGN PATENT DOCUMENTS

CN 106222085 A 12/2016
CN 107351406 A 11/2017

OTHER PUBLICATIONS

Ozonefac, "Small Ozone Generator", Jan. 27, 2017, accessed at ozonefac.com on Aug. 20, 2019. (Year: 2017).*
(Continued)

*Primary Examiner* — Joseph S Del Sole
*Assistant Examiner* — Jamel M Nelson

(57) ABSTRACT

Method and apparatus for three dimensional printing/bio-printing is disclosed. The apparatus includes a chamber further comprising a housing, an air supply unit, a heating and cooling unit, a humidifier, printing heads, gas removal unit and inlets. The housing further includes a printing platform coated with an antibacterial material and a UV lamp and an ozone generator, configured to turn on before printing the three dimensional prints on the printing platform, in order to sterilize the housing. A positive pressure in the chamber is increased by the air supply unit and the gas removal unit. External gases are passed and adjusted into the chamber by inlets. The humidity and temperature in the chamber are adjusted by the humidifier and the heating and cooling unit. The printing heads dispense biomaterial on the printing platform to create a three dimensional print.

15 Claims, 9 Drawing Sheets

(51) Int. Cl.
- *B29C 64/112* (2017.01)
- *B29C 64/209* (2017.01)
- *B29C 64/245* (2017.01)
- *B29C 64/264* (2017.01)
- *C12M 1/26* (2006.01)
- *B29C 64/364* (2017.01)
- *B29C 64/393* (2017.01)
- *B33Y 50/02* (2015.01)
- *C12M 1/12* (2006.01)
- *C12M 1/00* (2006.01)
- *B33Y 80/00* (2015.01)
- *B33Y 10/00* (2015.01)
- *B33Y 40/00* (2020.01)
- *B33Y 70/00* (2020.01)

(52) U.S. Cl.
CPC ............ *C12M 33/00* (2013.01); *C12M 37/00* (2013.01); *C12M 41/14* (2013.01); *B29K 2995/0056* (2013.01); *B33Y 10/00* (2014.12); *B33Y 40/00* (2014.12); *B33Y 70/00* (2014.12); *B33Y 80/00* (2014.12)

(56) References Cited

U.S. PATENT DOCUMENTS

| 2018/0001567 A1* | 1/2018 | Juan ................ B22F 3/1055 |
| 2018/0126651 A1* | 5/2018 | Matsumura ........... B33Y 10/00 |
| 2018/0291602 A1* | 10/2018 | Schluttig ............... E03C 1/126 |
| 2018/0326665 A1* | 11/2018 | Gatenholm .............. B01L 1/02 |

OTHER PUBLICATIONS

International Search Report of PCT Patent Application No. PCT/CN2018/120751 dated Feb. 27, 2019.
http://www.poultryhub.org/most-popular/incubation, Poultry Hub, Physiology and Incubation.
H. H. Mitchell et al., The Chemical Composition of the Adult Human Body and Its Bearing on the Biochemistry of Growth, J. Biol. Chem., 1945, vol. 158, pp. 625-637.
Peter Esser et al., Evaporation from Cell Culture Plates, Thermo Fisher Scientific, 2011, Technical Bulletin: 02.

* cited by examiner

APPARATUS AND METHOD FOR THREE-DIMENSIONAL (3D) PRINTING/BIO-PRINTING

CROSS-REFERENCE TO RELATED APPLICATIONS AND PRIORITY

The present application claims priority from U.S. provisional application No. 62/597,901 filed on Dec. 12, 2017, the entirety of which is incorporated herein by a reference.

TECHNICAL FIELD

The present subject matter described herein, in general, relates to a field of three dimensional (3D) printing/bio-printing. In particular, the present subject matter relates to an apparatus and method for a three dimensional (3D) printing/bio-printing.

BACKGROUND

Three dimensional printing has been one of the most popular advanced technologies that have been employed in industries and biomedical research. A three dimensional bio-printing is one of the state-of-the-art technologies in which different materials or biomaterials can be deposited layer by layer to construct precise and detail micro-structure with a predetermined pattern and incorporating living cells. The printed "living" structure may produce different tissue models or organs having tremendous potential in research applications, regenerative medicines, and drug discoveries. According to the market research from Accuracy Research LLP, the market of three dimensional bio-printing is growing quickly with a CAGR of 16.7% per year. The market is expected to reach 9 billion USD by 2025.

The three dimensional bio-printing differs from the usual three dimensional printing in which living cells are used as ink. For cells to survive, optimal temperature, gas component, humidity parameters are required. When a three dimensional bio-printing is performed in an open space, the air that contains different kinds of impurities including, but are not limited to, bacteria, fungus, yeast, and virus causes serious contamination to cells cultures. Further, these impurities may grow at an exponential rate in nutrition-rich medium or hydrogel, which have been used in three dimensional bio-printing. Therefore, the existing three dimensional bioprinters available in the art are incomplete and non-feasible to end users because live cells do not survive at room temperature in the open space.

Thus, it is evident from that above that a proper control of printing environment is of significant importance for the specific conditions required by different printing materials and post-printing process, in particular, cell cultures in three dimensional printing. Thus, there is a long standing need of an improved apparatus for three-dimensional bio-printing and improved method thereof.

SUMMARY

This summary is provided to introduce concepts related to an apparatus and method for three-dimensional printing/bio-printing. This summary is not intended to identify essential features of the claimed subject matter nor is it intended for use in determining or limiting the scope of the claimed subject matter.

In one implementation, an apparatus for three-dimensional printing/bio-printing is disclosed. The apparatus may include a chamber, wherein the chamber is semi or fully closed and is enabled to maintain one or more predefined environmental parameters for cell culture and growth. The chamber may further include an air supply unit, a housing, one or more printing heads, a printing platform, one or more sterilizing means, one or more gas exchange units and a gas removal unit. The air supply unit may be configured to pull the air from the ambient environment and pass filtered air into the housing and wherein, the gas removal unit may be configured to remove impure air from the chamber thereby creating a positive pressure in the housing. The one or more gas exchange units may be configured to add and adjust an amount of external gases into the chamber during the printing of the three dimensional print. The housing may be configured to receive the filtered air and adapted to house the one or more printing heads, the printing platform and the one or more sterilizing means. The printing platform may be coated with an antibacterial material, wherein the printing platform is printed with a three dimensional print by dispensing biomaterials through the one or more printing heads. The sterilizing means may be configured to be turned on before printing the three dimensional prints in order to sterilize the housing. In one embodiment of the present implementation, the housing may further include a heating and cooling unit configured to heat and maintain temperature, at predefined measurement, inside the chamber, and a humidifier configured to generate water mist, thereby increasing the humidity in the chamber. In one embodiment, the chamber may further include a gas detector, wherein the gas detector is configured to detect the amount of air component inside the chamber and the external gases.

In another implementation, a method for printing a three dimensional print is disclosed. The method may include switching on a sterilizing means before printing a three dimensional structure in order to sterilize a housing, wherein the housing is adapted to house a three dimensional printer. The method may further include passing, via an air supply unit, the ambient environmental air into the housing. The method may include passing, via one or more gas exchange units, external gases into the chamber, wherein the one or more gas exchange units are further configured to add and adjust an amount of other gases into the chamber. The method may further include creating, a positive pressure by passing the filtered air via the air supply unit, into the housing and removing, via a gas removal unit, a small portion of air from the chamber.

The method may further include printing, via one or more printing heads, a three-dimensional print by disposing biomaterials on a printing platform, wherein the printing platform is coated with an antibacterial material. In one embodiment of the present implementation, the method may further include heating and cooling, via a heating and cooling unit, to heat and maintain temperature, at predefined measurement, inside the chamber. Further, the method may include generating, via a humidifier, water mist thereby increasing the humidity in the chamber. Furthermore, the method may include detecting, via a gas detector, the amount of air component inside the chamber and the external gases.

BRIEF DESCRIPTION OF THE DRAWINGS

The detailed description is described with reference to the accompanying figures. In the figures, the left-most digit(s) of a reference number identifies the figure in which the reference number first appears. The same numbers are used throughout the drawings to refer like features and components.

DETAILED DESCRIPTION

Reference throughout the specification to "various embodiments," "some embodiments," "one embodiment," or "an embodiment" means that a particular feature, structure, or characteristic described in connection with the embodiment is included in at least one embodiment. Thus, appearances of the phrases "in various embodiments," "in some embodiments," "in one embodiment," or "in an embodiment" in places throughout the specification are not necessarily all referring to the same embodiment. Furthermore, the particular features, structures or characteristics may be combined in any suitable manner in one or more embodiments.

Figure 1A:
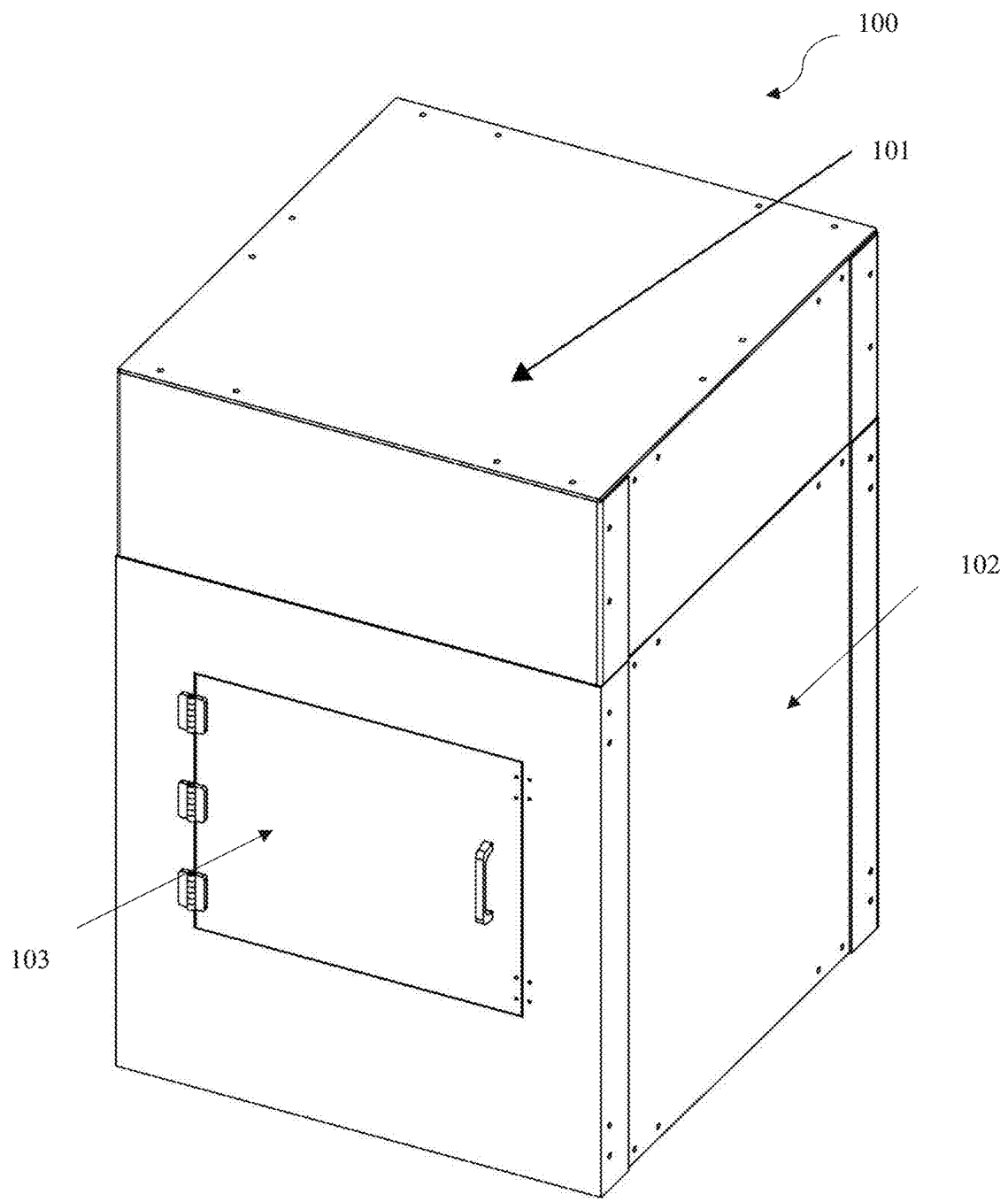
FIG. 1(a) and FIG. 1(b) illustrate, an apparatus 100 for three-dimensional printing, in accordance with an embodiment of the present application.
Figure 1B:
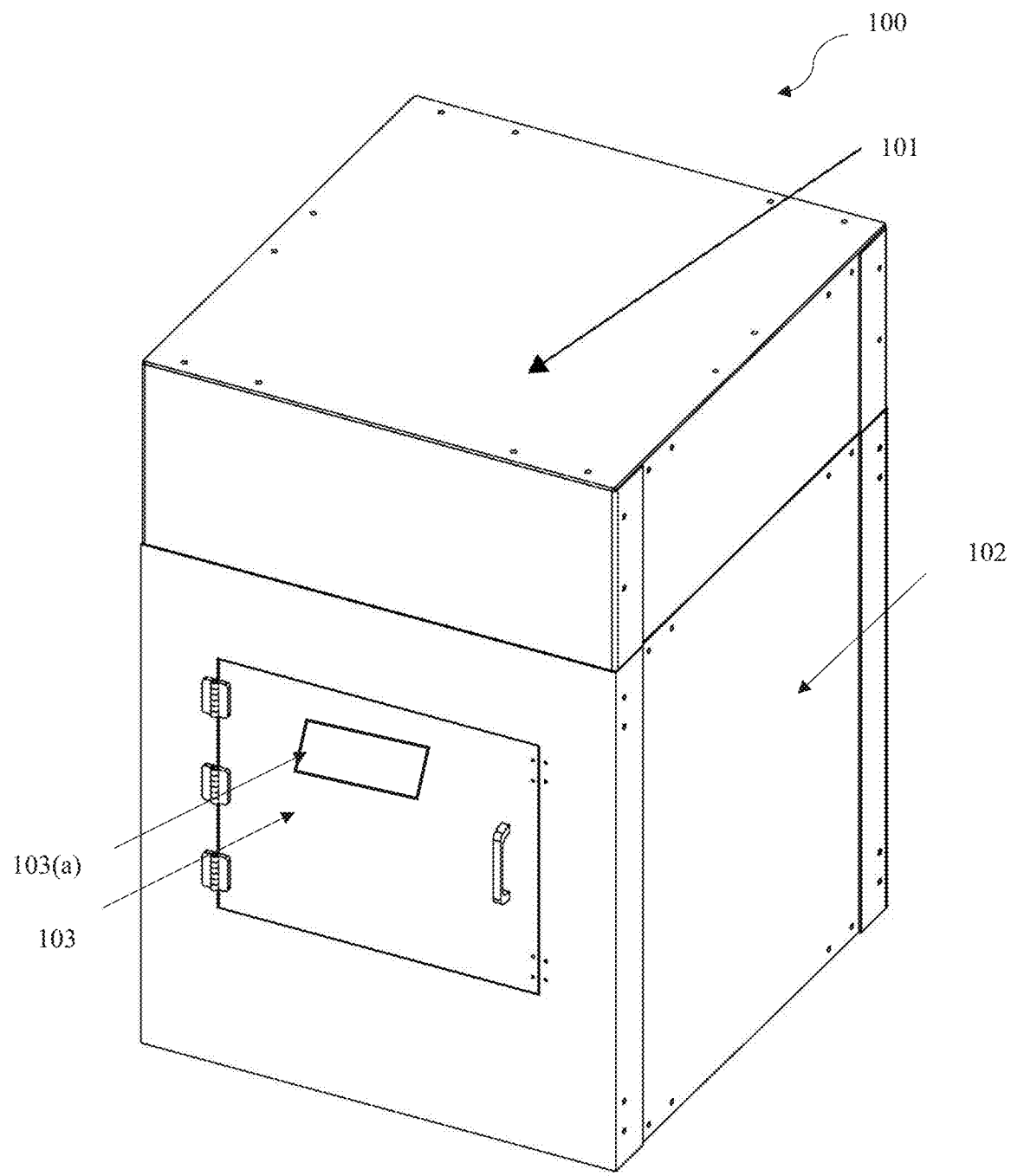

Referring now to FIG. 1(a) and FIG. 1(b), an apparatus 100 (also referred as "Vitality Chamber") for three-dimensional printing/bio-printing is illustrated in accordance with an embodiment of the present application. The apparatus 100 may include a chamber 101 and a housing 102. In one embodiment, the chamber 101 may be semi or fully closed, wherein the chamber 101 may be enabled to maintain one or more predefined environmental parameters for cell culture and growth. The chamber 101 may be made of a metallic or plastic frame which may be configured to provide a full or relative airtightness to the chamber 101. Such a structure of the chamber 101 may create a stable and sterilized environment for three dimensional printing. The semi or fully closed chamber 101 provides sterile environment three dimensional bio-printing of human tissue models and organs and three dimensional cell culturing without requiring sterilized room facilities. In one embodiment, the apparatus 100 for printing the three dimensional prints may be configured for producing cell, tissue, organ scaffold and such like. In one embodiment, the chamber 101 may include at least one three dimensional printer, pressure pump, sterile internal needle, septum, air circulator micro spray nozzle connected to a spray pump and such like.

In an embodiment, the chamber 101 may include a housing 102 defining a sterilized, temperature and humidity adjustable interior with the introduction of external gases into the housing 102. The housing 102 may be adapted to house a three dimensional printer or a three dimensional bio-printer. The housing 102 may include a sealing system around the windows and doors 103 to make the housing airtight. The housing 102 may be constructed of materials which include, but may not be limited to one or more of steel, stainless steel, aluminum, titanium, glass, or plastic, or any combination thereof. The housing 102 may have a volume that is around than 1 m3. In embodiments, the housing 102 further may include one or more controls or displays, ports for cables enabling interfacing with the three dimensional bio-printer. The cables may comprise but may not be limited to power cables, USB cables and such like. The housing 102 may further include a door 103 adapted for providing access inside the housing 102 and at least one window 103a adapted for viewing inside the housing 102. In some embodiments, the housing 102 may provide transparent windows and doors 103 (as shown in FIG. 1(a)) for viewing or access to various components of the three dimensional bio-printer. For example, the windows and door may provide viewing or access to components such as motors, printing heads, print beds, substrates for printing, printed structures, cartridges, syringes, platforms, lasers and controls. The transparent windows may be made of glass, plexiglass, plastic, or the like. Alternatively, or in addition, doors 103 may be provided which allow the operator to insert or remove materials inside the chamber 101. The doors 103 may be configured to minimize the introduction of particulate matter inside the chamber. The doors 103 may have an airtight sealed closed position, or an open position which allows access to the three dimensional printer or bio-printer. In the open position, the positive pressure environment inside the chamber 101 may ensure that no contaminants are introduced inside the chamber 101. The doors or ports are optimally positioned to allow access to various components of the three dimensional printer or bio-printer that may need removal or replacement, such as syringes containing printing materials, or three dimensional printed materials from the print bed of the printer. The doors 103 or ports may also provide access to operating controls of the printer. Additionally, the chamber 101 may be integrated with the three dimensional printer or bio-printer in a manner which allows for operation of the three dimensional printer while maintaining a sterilized air environment.

In another embodiment, the controls of the three dimensional printer are provided outside the housing 102 of the chamber 101 and transmit commands to the three dimensional printer/bio-printer. In this way, the three dimensional printer/bio-printer is controlled without an operator having to breach the airtight housing to control the printer. Alternatively, the housing 102 may have USB ports which are wired to the three dimensional printer, and the three dimensional printer may be controlled through a computer, motherboard or processor (not shown in the figure) connected to the housing 102 through the USB ports. A memory (not shown in figure) may be coupled to the processor, wherein the memory may be configured to store instructions which are executed by the processor. In one embodiment, the memory may store necessary data of predefined environmental parameters such as temperature, humidity, oxygen, carbon dioxide content, as well as factors for required for a pathogen-free environment. These factors allow and promote the growth of cells, prevent pre-mature dying, and prevent contamination of the cells during the long printing process. A firmware may be installed in the computer of the three dimensional printer and may be programmed to control the speed of the components of the apparatus 100 such as fans or blowers and the like. In one embodiment, a micro controller and a metal-oxide-semiconductor field-effect transistor or any other type of transistor used for amplifying or switching electronic signals in the apparatus 100. Alternatively, the speed of the fan or blower may be controlled through the software interface in an external computer device. The air flow speed, high efficiency filter life cycle and particle count in the chamber 101 may be displayed on a touch-screen or LCD display on the three dimensional printer and in the software interface. In one embodiment, the apparatus 100 may comprise a three dimensional bio-printer, as well as various reagents and consumables for use in the three dimensional bio-printer such as hydrogels, syringes, binding agents, cells, multiwell plates, Petri dishes, replacement filters, and the like.

Figure 2:
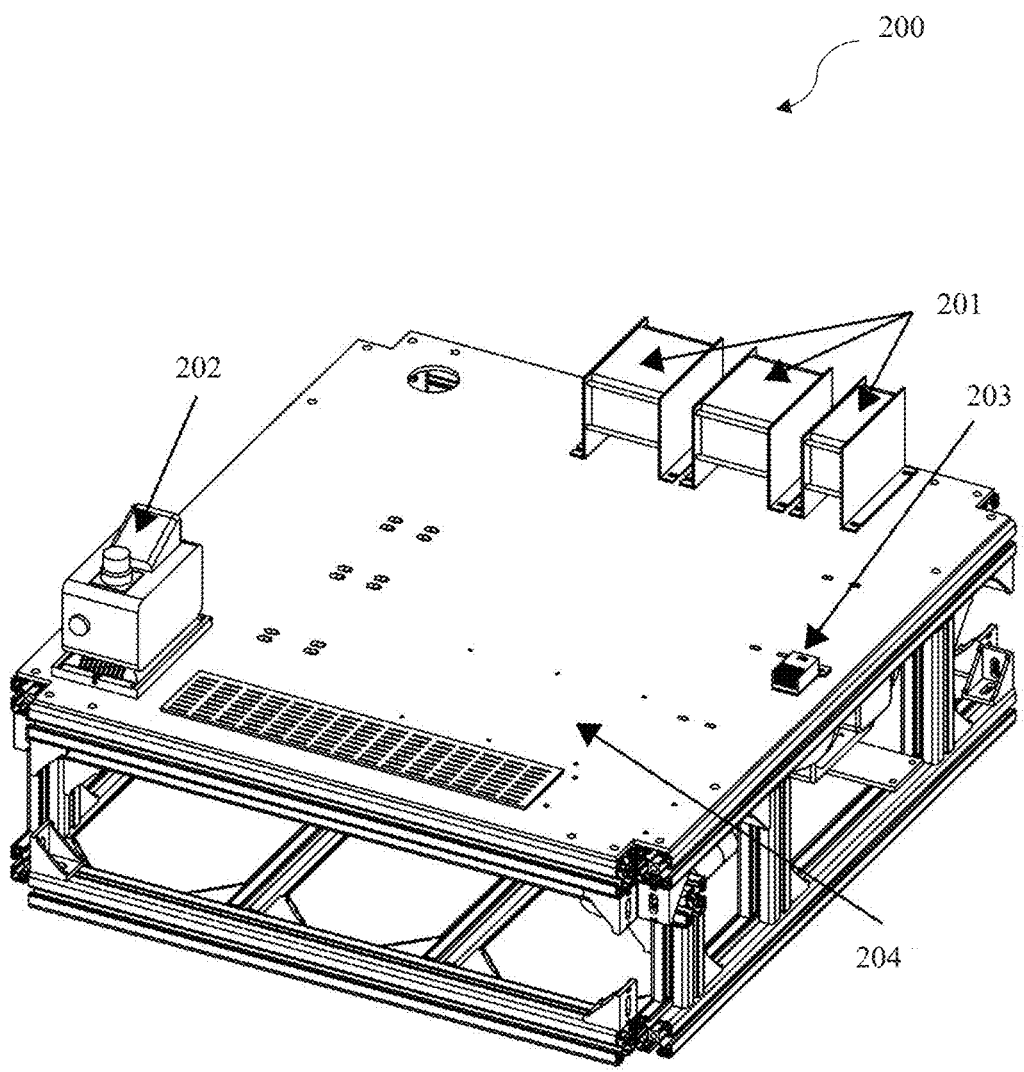
FIG. 2 illustrates, a perspective view 200 of a printing platform 204 of the apparatus 100 for printing the three dimensional prints, in accordance with an embodiment of the present application.

Referring now to FIG. 2, a perspective view 200 of a printing platform 204 of the apparatus 100 for printing the three-dimensional prints, is illustrated in accordance with an embodiment of the present application. The printing platform 204 may be comprised in the housing 102. The printing platform 204 may be coated with an antibacterial material. In one embodiment, the printing platform 204 may be configured as or enclosed in a sliding access door or tray that allows removal of three dimensional printed products. The printing platform 204 may comprise a heating and cooling unit 201, a humidifier 202, and a gas detector 203. In one embodiment, the housing 102 may include one or more fluid sources (not shown in figure) adapted for three dimensional printing or bio-printing, wherein said fluid sources are disposed above the printing platform. In one embodiment, the printing platform 204 may be disposed between an air supply unit 301 (shown in FIG. 3) and gas removal unit 400 (shown in FIG. 4). The printing platform 204 may be configured to print living cells, tissues organs and such like. In one embodiment, the humidifier 202 may be configured to generate water mist. The heating and cooling unit 201, may be configured to maintain temperature inside the chamber 101, to a predefined level, wherein the temperature may be sensed by temperature sensors and similarly humidity may be sensed by humidity sensors (not shown in figure). The gas detector 203 may be configured to detect the amount of air component inside the chamber 101 including but not limited to carbon dioxide, oxygen, nitrogen, and argon.

In one embodiment, a temperature and humidity sensor (not shown in figure) may be used to provide feedback to the heating and cooling unit 201 and a humidifier 202 in order to provide a desired temperature and humidity environment within the chamber 101. The temperature of the chamber 101 may vary from 0° C.-50° C.

Now referring to FIG. 1(a), FIG. 1(b) and FIG. 2, in one embodiment, the housing 102 may comprise one or more printing heads (not shown in figure) for printing eukaryotic and prokaryotic cells within, on and without hydrogels. The printing may be performed on the printing platform 204. In one embodiment, the printing heads may dispense biomaterials with dynamic viscosity ranges of 1 to 20,000,000 centiPoise (cP). The printing heads may be used to dispense biomaterials, hydrogels, materials prepared from decellularized human and animal tissues and organs, as well as cells in suspension in a defined and non-defined pattern. The printing heads are capable of dispensing these biomaterials to create a three dimensional structure, including those containing eukaryotic and prokaryotic cells. In various embodiments, the housing 102 may contain printing heads from 1 to 20. The printing heads may be positioned apart from each other with a distance of between 1 mm to 100 mm. The printing heads may dispense material such as bioinks through needles with straight or conical tips (not shown in figure) and co-axial needles. The bioinks can be mixed with human cells prior to dispensing. The printing platform 204 may be provided in order dispense the material on a removable substrate or directly on top of the printing platform 204 itself. The printing platform 204 may hold Petri dishes, multi well plates, and/or glass slides. Said materials may be dispensed using pneumatic pressure, mechanical pressure, heated extrusion, hydraulic extrusion, or pneumatic extrusion, or by way of a jet printer with piezoelectric applicator or jet dispenser with pneumatic applicator. In embodiments, the printing heads and printing platform 204 are positioned in the housing 102, below a high efficiency filter 303 (shown in FIG. 3) so that the print beds may directly receive filtered air entering the housing 102 and chamber 101. The filtered air and positive pressure created inside the chamber 101 allows for sterile printing of cell-laden and cell-free three dimensional structures. For example, the printing platform 204 of the apparatus 100 may be configured as or enclosed in an access door 103 or tray that allows removal of three dimensional printed products. The positive pressure environment maintained by the air supply unit 301 ensures that unfiltered air does not enter the sterilized chamber 101 when the door 103 or other ports are open. In one embodiment, the door 103 may be sliding.

Figure 3:
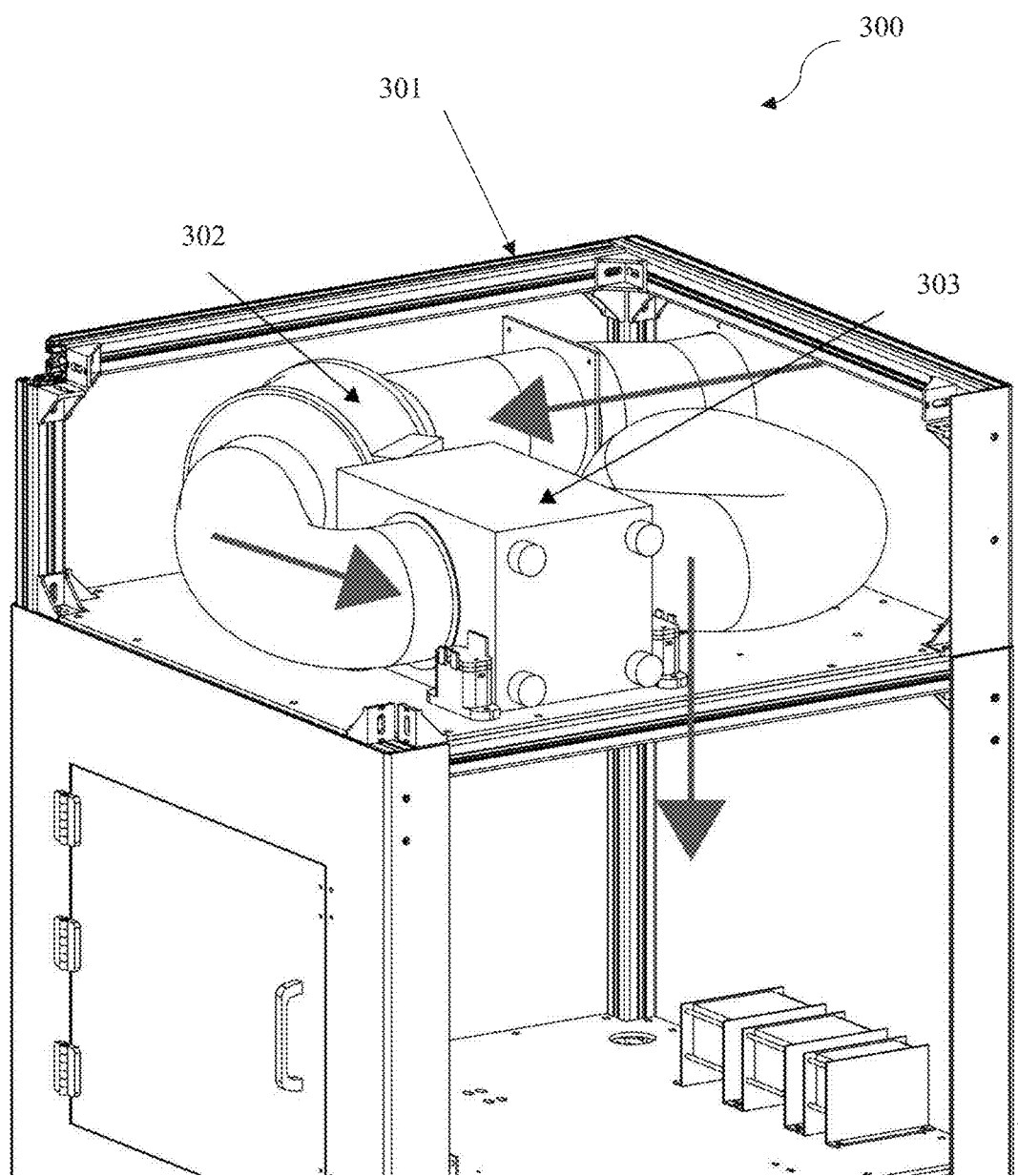
FIG. 3 illustrates, a perspective view 300 of an air supply unit 301, of the apparatus 100 for printing the three dimensional prints, in accordance with an embodiment of the present application.

Referring now to FIG. 3, a perspective view 300 of an air supply unit 301, of the apparatus 100 for printing the three-dimensional prints, is illustrated in accordance with an embodiment of the present application. The air supply unit 301 may comprise a fan 302 and a filter 303. The fan 302 may pull the air from the ambient environment and pass the said air to the filter 303, into the housing 101. This makes sure that the air inside the chamber is purified before the three dimensional printing and also a positive pressure is created in the housing 102. Thus, a positive pressure environment maintained by the air supply unit 301 ensures that unfiltered air does not enter the housing 102 when the door 103 or other ports are open. In one embodiment, the filter 303 may comprise filters such as a HEPA filter or an ULPA filter and such like.

In one embodiment, the chamber 101 may include one or more air supply units 301 and one or more vents (not shown in figure). The air supply units 301 may be disposed at the top of the housing 102 and the one or more vents may be disposed at the sides or the bottom of the housing 102. Thus, the air supply units 301 and one or more vents may provide vertical laminar air flow which is disposed above the printing platform 204. The air supply units 301 and one or more vents are configured to provide positive pressure inside the housing, such as a positive pressure differential of 0.02 in. to 0.2 in water column.

Figure 4:
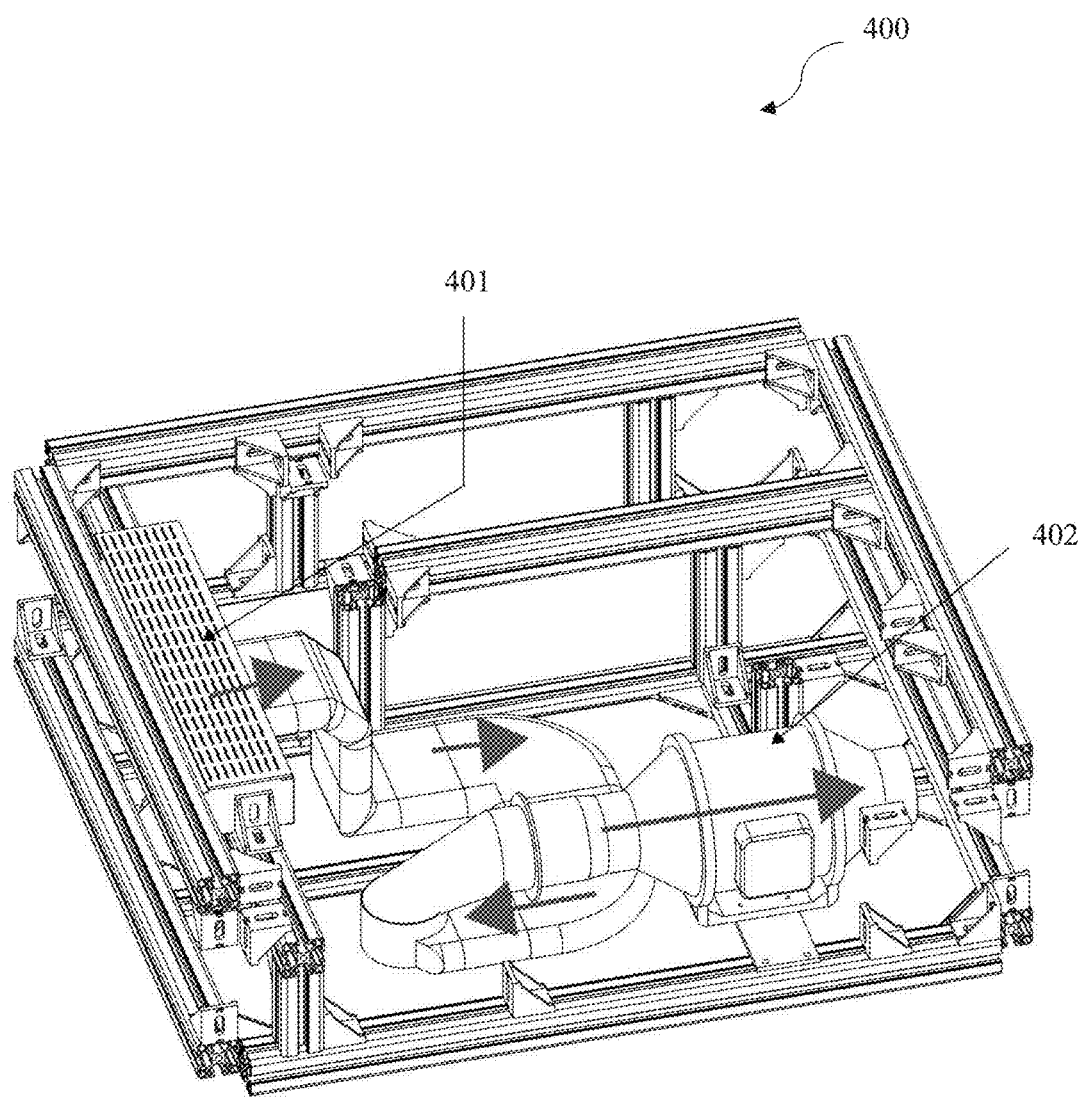
FIG. 4 illustrates, a gas removal unit 400, of the apparatus 100 for printing the three dimensional prints, in accordance with an embodiment of the present application.

Referring now to FIG. 4, a gas removal unit 400, of the apparatus 100 for printing the three-dimensional prints, is illustrated in accordance with an embodiment of the present application. The gas removal unit 400 may comprise a gas removal filter 401 and a gas removal fan 402. In one embodiment, the gas removal filter 401 may be configured to remove a small portion of the filtered air from the interior of the apparatus 100. Thus, the gas removal unit may be configured to remove air from the chamber 101, thereby creating a positive pressure in the housing.

Figure 5:
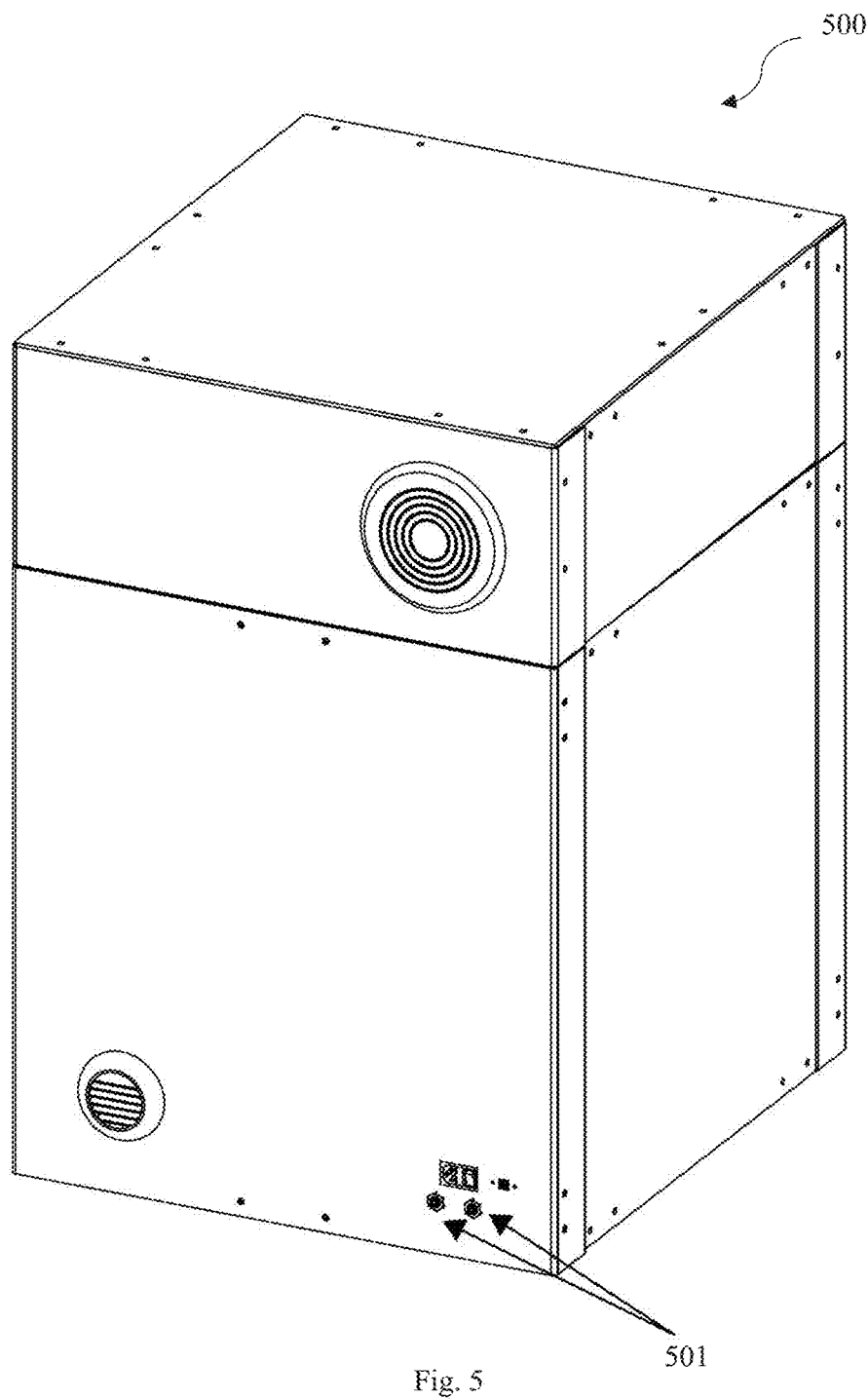
FIG. 5 illustrates, a rear view 500, of the apparatus 100 for printing the three dimensional prints, in accordance with an embodiment of the present application.

Referring now to FIG. 5, a rear view 500 of the apparatus 100 for printing the three dimensional prints, is illustrated in accordance with an embodiment of the present application. In one embodiment, the apparatus 100 may comprise one or more gas exchange units 501. In one embodiment, the one or more gas exchange units 501 may be configured to allow addition of other gases into the chamber 101. In one embodiment, the one or more gas exchange units 501 may be configured to add and adjust the amount of other gases into or outside the chamber 101.

In embodiments, external gases may be applied into the chamber 101 including but not limited to CO2, NO2, O2, Ar, N2, CO, but varies in percentages ranging from 0-50%. In one embodiment, the gas detector 203 may support the adjustment of the one or more gas exchange units 501 to control the amount of gases entering the chamber 101.

Figure 6:
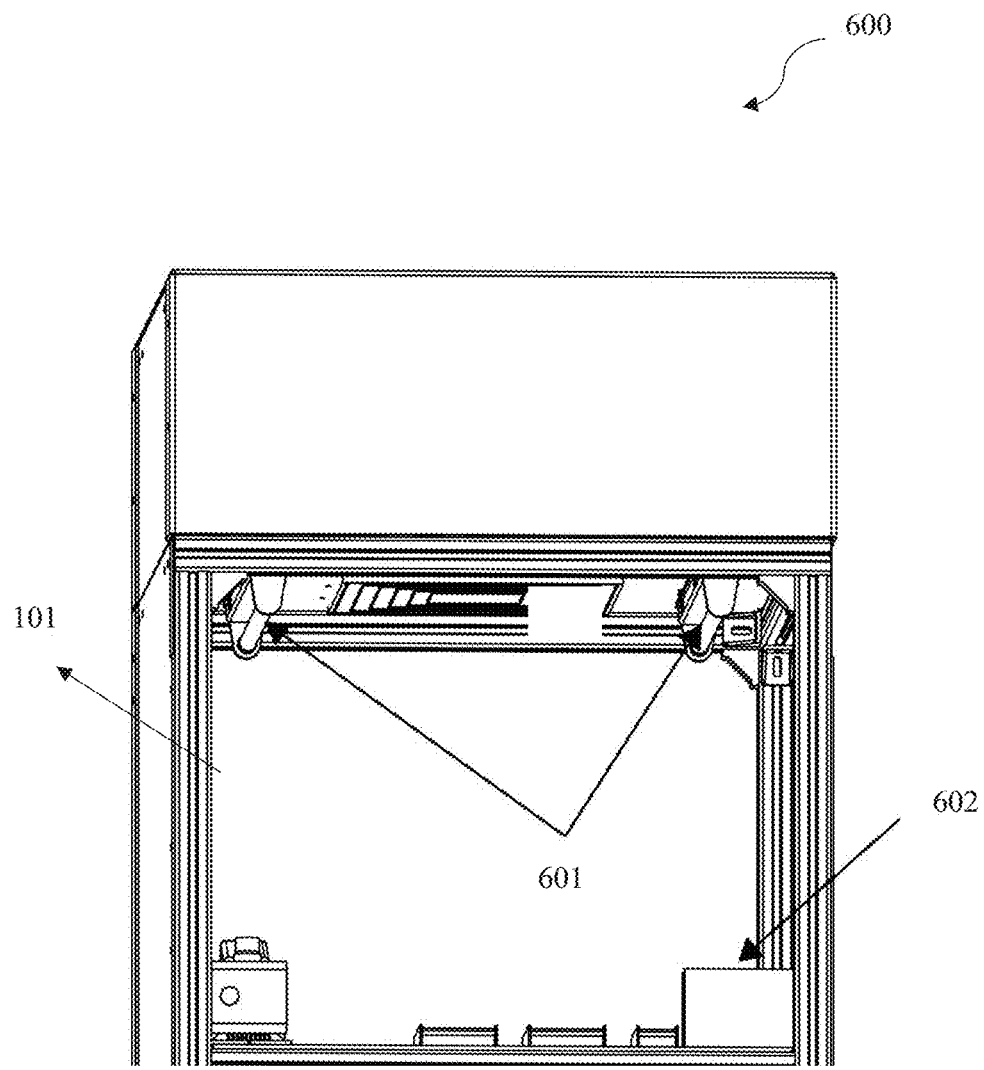
FIG. 6 illustrates, an internal view 600, of the housing 102, in accordance with an embodiment of the present application.

Referring now to FIG. 6, an internal view 600, of the housing 102, is illustrated in accordance with an embodiment of the present application. In one embodiment, the housing 102 may further comprise one or more sterilizing means such as an UV lamp 601 and an ozone generator 602. The UV lamp 601 and the ozone generator 602, may be turned on before printing the three dimensional prints in order to sterilize the housing 102. In one embodiment, the housing 102 may be equipped with Ultraviolet C germicidal lamp with a wavelength ranging from 100-280 nm, and potential ranging from 4.43-12.4 eV, to sterilize the interior of the housing 102, more particularly the printing platform 204, before usage in order to prevent contamination by inactivating bacteria, viruses, and protozoa that may enter the housing 102. In one embodiment, the housing 102 may contain a UV curing light with wavelength ranging from 300 nm to 500 nm as well as a UV light for sterilization of the printing area.

In some embodiments, the apparatus 100 may include a UV lamp, HEPA filters, antimicrobials surface coating, and an ozone generator, working together to keep the chamber 101 and housing 102 sterilized. Further, components including temperature and humidity control system provide optimal environment for the living cell growth and culture, while a gas inlet and detector allows the additional of external gases to fits users' specific needs. As organisms, tissue and organ can only survive in a specific condition, the apparatus 100 for three-dimensional printing is able to provide a filtered air and close environment system to keep the area inside the chamber to be contamination free before or after printing for a precision of time for their post processing.

Figure 7A:
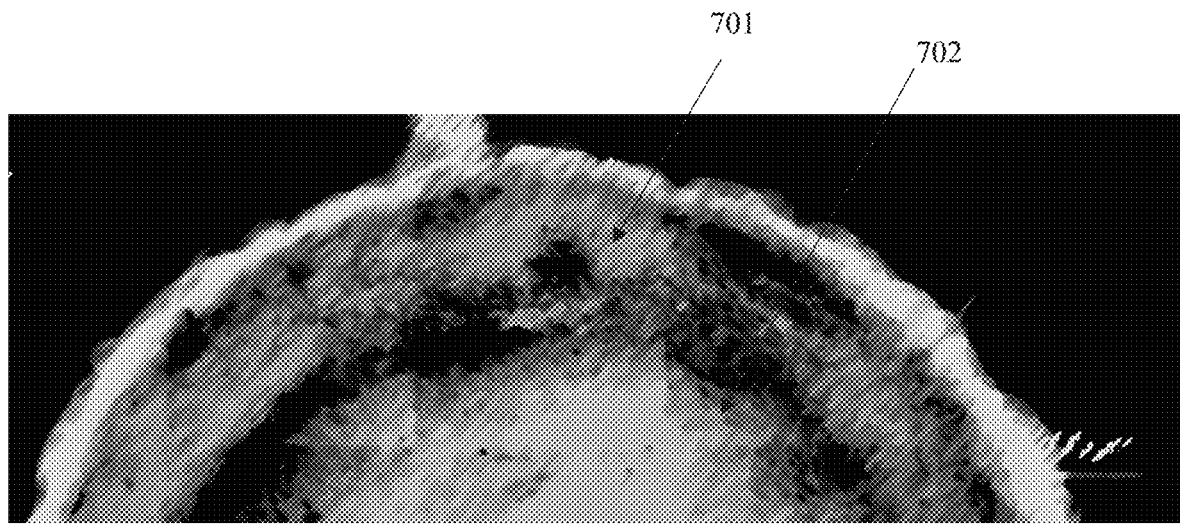
FIG. 7(a) and FIG. 7(b) illustrates, results depicting a contamination free bio-print and a contaminated bio-print, respectively, in accordance with an embodiment of the present application.
Figure 7B:
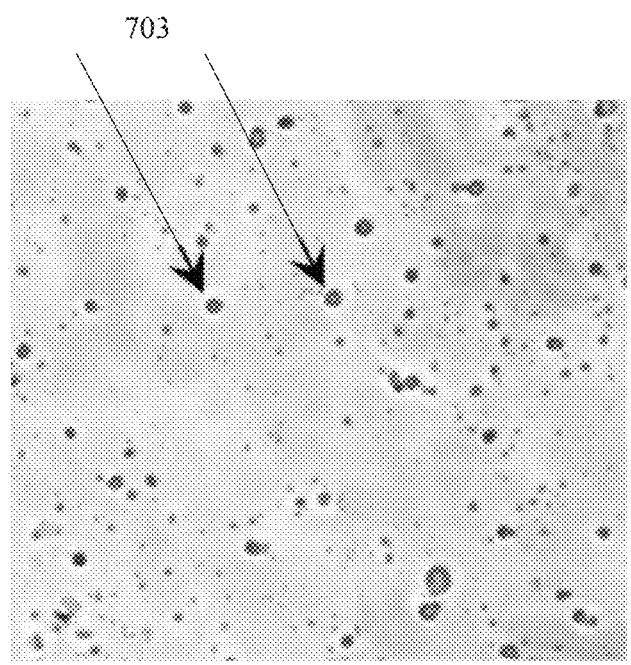

FIG. 7(a) and FIG. 7(b) illustrate results depicting a contamination free bio-print and a contaminated bio-print, respectively, in accordance with the present subject matter. FIG. 7(a) and FIG. 7(b) depict both conditions when the apparatus 100 for three dimensional printing was used and was not used. Referring to FIG. 7(a), a microscopy image indicating a successful printing of a bio-print is depicted. Here, the outer portion 701 and the inner portion 702 represent two types of cells that are alive and printed in a defined scaffold. Referring to FIG. 7(b), an image of a contaminated printing is depicted. Here a plurality of dying cells 703 were observed and no fluorescent signal was observed.

It is to be noted that cellular functions are highly responsive to temperature. As an example, chick embryos show increased mortality with a difference of only 1° C.(1). Metabolism and growth slow down at lower temperatures. It is also important not to overshoot the set temperature, because higher temperatures are even more detrimental. As far as the ideal temperature for cell growth is concerned, it is mainly dependent on the cell types.

For most mammalian cells thrive at around 37° C.

Insect cells require lower temperatures of approximately 27° C. for optimal growth Avian cell lines normally require 38.5° C. for maximum growth 'Cold-blooded' animals (e.g., amphibians, cold-water fish) can be cultured anywhere between 15° C. and 26° C.

In an embodiment, $CO_2$ gas works with sodium bicarbonate in the growth medium to control pH to a neutral 7.4. This mimics bloodstream biochemistry. When the pH varies from neutral, cells will first stop growing and then lose viability. Improper pH may produce morphological changes such as vacuoles in the cytoplasm or granules around the nucleus. The concentration of $CO_2$ will be mainly dependent on the cell types and keep the PH as mentioned above.

The human body is about 60% water, with internal organs 75-80% water (2). In a cell culture incubator, balanced growth media provide moisture and nutrients for cells. Humidity of 85-95% limits evaporation of water from the media. Evaporation leaves too-high concentrations of salts, minerals, etc., resulting in toxicity and cell death. High humidity is the most difficult condition to reestablish but is critically important, as evaporation is 4 times faster at 80% humidity than at >93% (3). The humidity to be kept will be around 85-95% inside the chamber 101.

Figure 8:
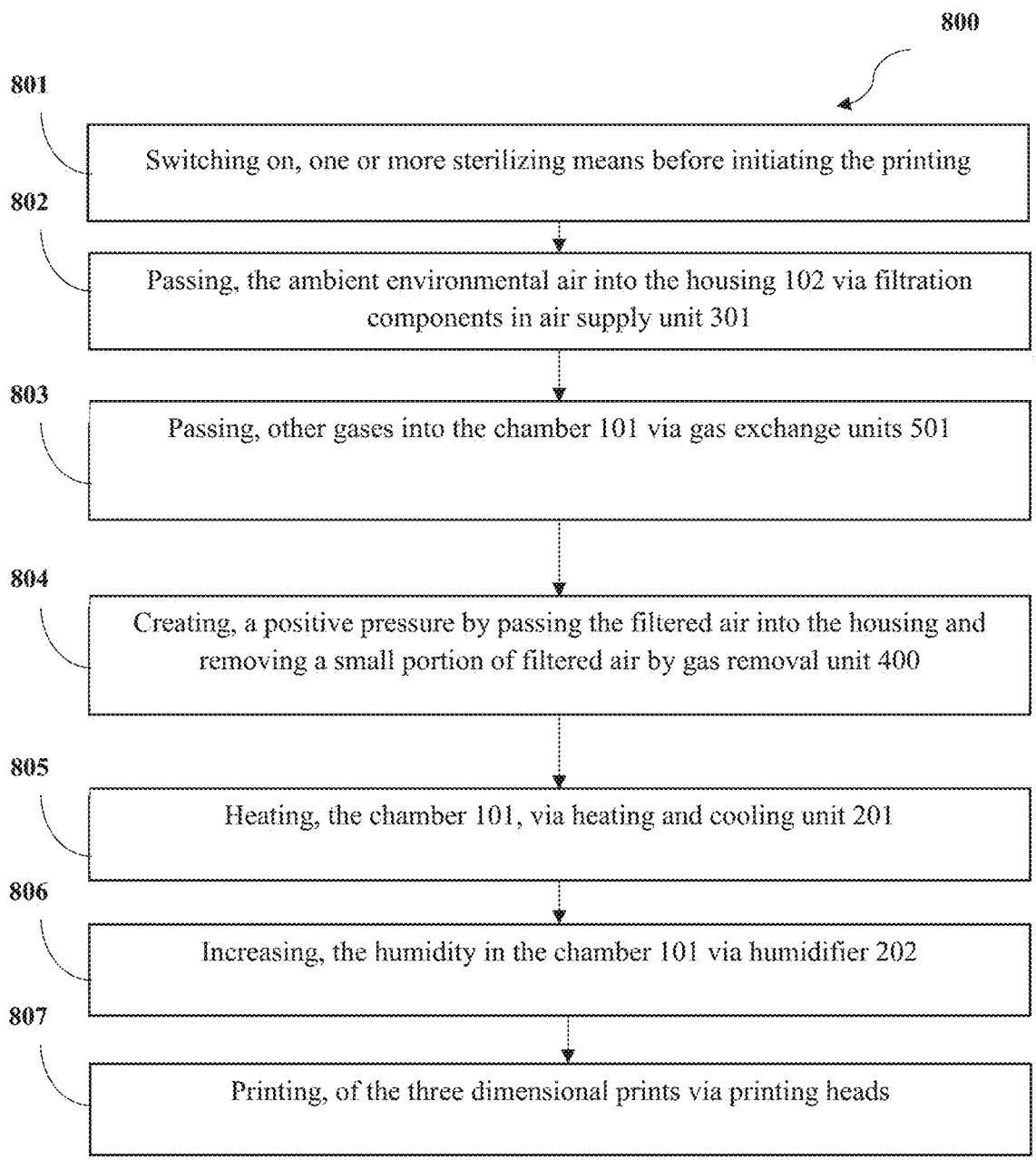
FIG. 8 illustrates, a method 800 for printing the three dimensional prints, in accordance with an embodiment of the present application.

Referring now to FIG. 8, a method 800 for printing the three-dimensional prints, is illustrated in accordance with an embodiment of the present application. At step 801, the sterilizing means such as the UV lamp 601 and ozone generator 602 may be switched ON before initiating the printing of three dimensional structures, in order to sterilize the housing.

At step 802, the ambient air from the environment, may be pulled and passed into the housing 102 via filter 303 positioned in the air supply unit 301.

At step 803, other gases may be allowed in pass inside the chamber 101. The gas exchange units 501 may be configured to allow addition of other gases into the chamber 101. In one embodiment, said gas exchange units 501 may be configured to add and adjust the amount of other gases into or outside the chamber 101.

At step 804, a positive pressure may be created. In one embodiment, an air supply unit 301 may be configured to pull and pass the air from the ambient environment into the housing 102. The filter 303, positioned in the air supply unit 301, may be configured to filter the ambient air and the pass the air to the housing 102. Simultaneously, the removal of filtered or pure air may be performed. The gas removal unit 400 may be configured to perform gas removal from the chamber 101. Thus, a positive pressure may be created by passing the filtered air into the housing and removing a small portion of filtered air via gas removal unit 400. At step 805, warming or heating of the chamber 101 may be performed. In one embodiment, the heating and cooling unit 201 may be configured to warm and maintain temperature, at predefined measurement, inside the chamber 101, wherein the temperature may be sensed by temperature and humidity sensors.

At step 806, increasing the humidity in the chamber 101 may be performed. In one embodiment, the humidifier 202 may be configured to generate water mist, thereby increasing the humidity in the chamber 101.

At step 807, printing of the three dimensional prints may be performed. In one embodiment, the printing heads (not shown in figure) may be capable of dispensing biomaterials to create a three dimensional structure. In one embodiment, the printing heads may be mounted in the housing. The dispensed biomaterial may be disposed on the printing platform 204 on a removable substrate or directly on top of the printing platform 204 itself.

Although implementations for apparatus and method for three-dimensional printing have been described in language specific to structural features and/or methods, it is to be understood that the appended claims are not necessarily limited to the specific features or methods described. Rather, the specific features and methods are disclosed as examples of implementations for three-dimensional printing.

What is claimed is:

1. An apparatus for three-dimensional bio-printing, comprising:
    a chamber, wherein the chamber is semi or fully closed and is enabled to maintain one or more predefined environmental parameters for cell culture and growth, wherein the chamber further comprises an air supply unit, a housing, one or more printing heads, a printing platform, sterilizing means comprising an UV lamp along with an ozone generator, a gas detector, one or more gas exchange units and a gas removal unit wherein the gas removal unit further comprises a gas removal filter and a gas removal fan;
    wherein the air supply unit is configured to pull the air from the ambient environment and pass filtered air into the housing, and wherein the gas removal unit is configured to remove a small portion of filtered air from the chamber, thereby creating a positive pressure in the housing;
        wherein the one or more gas exchange units are configured to add and adjust an amount of external gases into the chamber during the printing of the three dimensional print;
        wherein the housing is configured to receive the filtered air and adapted to house the one or more printing heads, the printing platform and the one or more sterilizing means;
        wherein the printing platform is coated with an antibacterial material, wherein the printing platform is printed with a three dimensional print by dispensing biomaterials through the one or more printing heads;
        wherein the gas detector is configured to detect the amount of air component inside the chamber and the external gases, wherein the external gases detected comprises carbon dioxide, oxygen, nitrogen, carbon monoxide, nitrogen dioxide and argon;
        wherein the one or more gas exchange units are configured to add and adjust the amount of external gases into the chamber based upon the amount of air component inside the chamber and the external gases detected by the gas detector;
        wherein the UV lamp along with the ozone generator are configured to be turned on before printing the three dimensional prints in order to sterilize the housing; and
    wherein the gas removal filter is configured to remove a small portion of filtered air from the chamber.

2. The apparatus of claim 1, wherein the housing further comprises a heating and cooling unit configured to heat and maintain temperature, at predefined measurement, inside the chamber, and a humidifier configured to generate water mist, thereby increasing the humidity in the chamber.

3. The apparatus of claim 1, wherein the housing comprises USB ports wired to a three dimensional printer and controlled through a computer comprising a processor and memory, wherein the memory is coupled to the processor and configured to store data for printing and instructions capable of being executed by the processor.

4. The apparatus of claim 3, wherein the data comprises predefined environmental parameters comprising one or more of temperature, humidity, oxygen, carbon dioxide content, and factors required for a pathogen-free environment.

5. The apparatus of claim 1, wherein the chamber is made of a metallic or plastic frame which may be configured to provide a full or relative airtightness to the chamber.

6. The apparatus of claim 3, wherein the housing is made of steel, stainless steel, aluminum, titanium, glass, or plastic, or any combination thereof, wherein the housing has a volume around 1 $m^3$, wherein the housing further comprises one or more controls or displays, and ports or cables for interfacing with the apparatus for three dimensional printing.

7. The apparatus of claim 6, wherein the housing comprises at least one door and a window for providing access and viewing inside the housing.

8. The apparatus of claim 7, wherein the at least one door and window are transparent.

9. The apparatus of claim 2, wherein the heating and cooling unit, is configured to maintain temperature inside the chamber at a predefined range of 0° C. 50° C., wherein the temperature is sensed by one or more temperature sensors.

10. The apparatus of claim 1, wherein the one printing heads dispenses the biomaterials having dynamic viscosity within a range of 1 to 20,000,000 centiPoise (cP), and wherein the one or more printing heads vary in a range of 1 to 20, and wherein the one or more printing heads are positioned apart from each other with a distance of between 1 mm to 100 mm.

11. The apparatus of claim 10, wherein the printing platform allows dispensing of the biomaterials on a removable substrate or directly on top of the printing platform.

12. The apparatus of claim 1, wherein the air supply unit comprises a fan and a filter, wherein the fan pulls the air from the ambient environment and pass the said air through the filter, into the housing.

13. The apparatus of claim 12, wherein the filter comprises a HEPA filter or an ULPA filter.

14. The apparatus of claim 1, wherein the positive pressure of 0.02 in to 0.2 in water column is created.

15. The apparatus of claim 1, wherein the sterilizing means comprise a UV lamp and ozone generator, and wherein the UV lamp comprises Ultraviolet C germicidal lamp having a wavelength within a predefined range of 100-500 nm and a potential within a predefined range of 4.43-12.4 eV.

* * * * *